(12) United States Patent
Knox

(10) Patent No.: US 8,412,481 B2
(45) Date of Patent: Apr. 2, 2013

(54) METHOD AND APPARATUS FOR DETERMINING OPERATIONAL CONDITION OF POLLUTION MONITORING EQUIPMENT

(75) Inventor: Ron Knox, Mount Eliza (AU)

(73) Assignee: Vision Fire & Security Pty Ltd, Victoria (AU)

( * ) Notice: Subject to any disclaimer, the term of this patent is extended or adjusted under 35 U.S.C. 154(b) by 567 days.

(21) Appl. No.: 10/595,193

(22) PCT Filed: Sep. 24, 2004

(86) PCT No.: PCT/AU2004/001320
§ 371 (c)(1),
(2), (4) Date: Oct. 30, 2006

(87) PCT Pub. No.: WO2005/029435
PCT Pub. Date: Mar. 31, 2005

(65) Prior Publication Data
US 2007/0168140 A1 Jul. 19, 2007

(30) Foreign Application Priority Data
Sep. 24, 2003 (AU) ................ 2003905197

(51) Int. Cl.
*G01F 25/00* (2006.01)
(52) U.S. Cl. ....... 702/116; 701/100; 73/1.16; 73/861.28
(58) Field of Classification Search ............ 702/45, 702/116, 100; 73/1.05, 1.16, 863.03, 861.28, 73/53.01
See application file for complete search history.

(56) References Cited

U.S. PATENT DOCUMENTS

| 3,693,401 | A | | 9/1972 | Purt et al. |
| 4,569,235 | A | * | 2/1986 | Conkle et al. ............ 73/863.03 |
| 5,477,218 | A | | 12/1995 | Manmoto et al. |
| 5,533,408 | A | * | 7/1996 | Oldenziel et al. ......... 73/861.18 |
| 6,439,062 | B2 | * | 8/2002 | Stark et al. ................ 73/861.77 |
| 6,679,103 | B1 | | 1/2004 | Sadler |
| 2001/0004842 | A1 | * | 6/2001 | Krajewski et al. ............ 73/1.16 |

FOREIGN PATENT DOCUMENTS

| DE | 19605637 | 5/1997 |
| EP | 0 197 371 | 3/1986 |
| FR | 2 254 073 | 8/1975 |
| FR | 2551215 | 3/1985 |
| GB | 2 140 163 A | 11/1984 |
| JP | 9-196843 | 7/1997 |
| SU | 989271 | 1/1983 |
| WO | WO 96/07166 | 3/1996 |
| WO | WO 00/03224 | 1/2000 |
| WO | 03069571 | 8/2003 |

OTHER PUBLICATIONS

Patent Abstracts of Japan JP 11-224386 A (Hochiki Corp); Aug. 27, 2002.

* cited by examiner

*Primary Examiner* — Bryan Bui
(74) *Attorney, Agent, or Firm* — Sughrue Mion, PLLC

(57) ABSTRACT

A method for determining an operational condition of a particle detection system including at least one sample inlet for receiving a sample flow from a monitored region. The method includes the step of conducting an upstream measurement of a flow rate through the at least one sample inlet.

26 Claims, 3 Drawing Sheets

METHOD AND APPARATUS FOR DETERMINING OPERATIONAL CONDITION OF POLLUTION MONITORING EQUIPMENT

RELATED APPLICATIONS

This application is a National stage under 35 U.S.C. §371 of PCT/AU2004/001320, with an international filing date of Sep. 24, 2004, which claims priority to Australian Provisional Patent Application No. 2003905197, filed 24 Sep. 2003 and entitled "Method and Apparatus for Testing Air Sampling Systems" and, the specification thereof is incorporated herein by reference in its entirety and for all purposes.

FIELD OF INVENTION

The present invention relates to a method and apparatus for determining the operational condition of pollution monitoring equipment. In particular, the present invention relates to a method and system for testing an operational condition of pollution monitoring equipment, which may comprise a particle detection system. In one form, the invention relates to a device and a method of conducting field testing of aspirated smoke detection systems by determining whether the particle detection system is detecting particles in a region adjacent a sampling inlet, and it will be convenient to hereinafter describe the invention in relation to that application. It should be appreciated, however, that the present invention is not limited to that application, only.

BACKGROUND OF INVENTION

The inventor has identified the following background and related art. Pollution monitoring, and fire protection and suppressant systems may operate by detecting the presence of smoke and other airborne pollutants. Upon a threshold level of particles being detected, an alarm may be activated and operation of a fire suppressant system may be initiated. While the fire itself will cause damage, considerable property damage and also environmental damage may also be caused by operation of the fire suppression system and subsequent removal of the suppressant may be quite hazardous. A detection system, which is sufficiently sensitive to detect an abnormal condition prior to the onset of a fire, is very advantageous as it enables action to be taken at a very early stage before the onset of actual fire conditions. For example, when most substances are heated, even before heating occurs to a point at which a fire commences, emissions will be generated and if these can be detected by a suitably sensitive system, a warning provided at that very early stage may allow the problem to be detected and rectified, or equipment turned off for example, before the fire actually starts.

Air sampling pollution monitoring equipment in the form of aspirated particle detection systems may incorporate a sampling pipe network consisting of one or more sampling pipes with sampling holes, or inlets, installed at positions where smoke or pre-fire emissions may be collected from a region or environment being monitored, which is ordinarily external to the sampling pipe network. Typical configurations for aspirated particle detection systems are shown in FIGS. 1 and 2 in the form of aspirated smoke detection systems 10 and 20, respectively. Air is drawn in through the sampling holes 14, 24 and subsequently along the pipe or pipe network 12, 22 by means of an aspirator or fan (not shown) and is directed through a detector 16 at a remote location. Sampling points in the form of the sampling inlets 14, 24 are located at regions where particle detection is required. These regions are typically distant from the actual detector. Although there are a number of different types of particle detectors which may be used as the detector in a system as outlined above, one particularly suitable form of detector for use in such a system is an optical scatter detector, which is able to provide suitable sensitivity at reasonable cost. An example of such a device is a VESDA® LaserPlus™ smoke detector as sold by the applicant. Optical scatter detectors operate on the principle that smoke particles or other airborne pollutants of small size, when introduced into a detection chamber and subjected to a high intensity light beam, will cause light to scatter. A light detector senses the scattered light. The greater the amount of particles within the sample introduced into the detector chamber the greater will be the amount of light scatter. The scatter detector detects the amount of scattered light and hence is able to provide an output signal indicative of the amount of smoke particles or other pollutant particles within the sample flow.

A difficulty arises in operation of aspirated particle detector systems of the above kind in that as the detector is remote from the sampling point, and the detector effectively detects particles from a number of sampling points simultaneously, it is difficult to ascertain whether any particular sample point is effectively sampling particles from the environment to be protected thus enabling the detection system to be capable of detecting particles. Furthermore, in some circumstances, one or more sampling points may block or be in a state of becoming blocked.

Smoke detectors, which do not use aspirated sampling pipe networks are also susceptible to failure; and are subject to other failure modes such as faulty electronic components. These detectors are commonly known as "point detectors" and often take the form of a detection chamber in a perforated housing located, for example, proximate to the potential site of a fire. The housings are typically protected to some extent from the ingress of dust, lint and insects and the like by a filter, which may comprise a fine mesh or other suitable barrier. These detectors rely on natural air movement through the region or environment being monitored by the detector for particles to enter through the mesh, but these detectors may become ineffective. Such point detectors are often tested in-situ when in operation in the field by enclosing them in a smoke-filled vessel holding a known concentration of smoke thus, ascertaining whether smoke will be detected in the monitored region. If the detector sounds the alarm then the detector is considered operational. Another method is to direct smoke or some other test medium such as a gaseous test material towards the detector to attempt to provoke an alarm.

U.S. Pat. No. 3,693,401 (Purt et al) and Patent Abstracts of Japan No. JP 11-224386 (Hochiki Corp) disclose devices for enclosing a smoke detector in a housing into which a test medium is sprayed and, directing a test gas at a smoke detector, respectively.

In another form of testing, U.S. Pat. No. 5,170,148 (Duggan et al) discloses a device that relies on the activation of a heating element to test the operational status of a fixed-temperature fire detector.

EP patent No 0910055 (No Climb Products Limited) discloses a test device that generates a stimulus by way of a non-contact detector to sense the presence of a smoke detector engaging the test device in order to initiate the test, which may involve the emission of an aerosol or the activation of a heating element. EP 0910055 also discloses a battery powered test apparatus mounted on the end of a hollow elongate member and means forming a battery retainer adjacent the mounting for the apparatus, which obviates the need for electrical cable from a power source, situated with the user, to a housing member located at the upper end of the elongate member for engaging the smoke detector.

However, the above methods are problematic when dealing with aspirated particle detectors. While the above test methods may be appropriate for non-aspirated point detectors, they present difficulties when applied to testing individual sampling points of aspirated detectors. In an aspirated sampling system as described above and shown in FIGS. 1 and 2, the alarm will be raised remotely at the detector, rather than in the region where testing is conducted. Further, producing and applying a test medium accurately in a number of different areas to test multiple sampling points is difficult, and results can therefore be difficult to analyse.

Any discussion of documents, devices, acts or knowledge in this specification is included to explain the context of the invention. It should not be taken as an admission that any of the material formed part of the prior art base or the common general knowledge in the relevant art on or before the priority date of the invention disclosed herein or, any claims defined herein.

SUMMARY OF INVENTION

In one aspect the present invention provides a method for determining an operational condition of a particle detection system, the particle detection system comprising at least one sample inlet for receiving a sample flow from a monitored region, the method comprising the step of:

conducting an upstream measurement of a flow rate through the at least one sample inlet.

In another aspect, the present invention provides a method of testing the operation of pollution monitoring equipment, the method comprising the steps of:

measuring the upstream flow rate through at least one sampling inlet of a particle detector system;

determining an operational condition of the pollution monitoring equipment in accordance with the measured flow rate.

Preferably, the method of testing further comprises the steps of:

repeating the step of measuring the upstream flow rate after a predetermined time interval;

determining the operational condition by comparing respective flow rate measurements.

The predetermined time interval may comprise one or more of:

the occurrence of an incident;
the occurrence of a maintenance action;
regular calendar periods.

The step of measuring the upstream flow rate, in the first instance, may be performed upon one of:

installation;
cleaning and;
repair of the pollution monitoring equipment.

In embodiments of the present invention, pollution monitoring equipment may comprise one or more of:

at least one sampling inlet of an aspirated particle detector system;
a particle detector;
a sampling pipe network of an aspirated particle detector system;
a portion of a sampling pipe network of an aspirated particle detector system;
an aspirated particle detector system.

In the above methods, the step of measuring the flow rate is preferably performed using an ultrasonic flow sensor. Furthermore, it is preferable that step of measuring the flow rate is performed at a point remote from the sampling inlet, at or near ground level.

According to embodiments of the invention, in the above methods, the operational condition that is determined may comprise one or more of:

a) particle detection system sensitivity;
b) particle detector sensitivity;
c) sampling pipe network obstruction;
d) sampling inlet obstruction.

In a further aspect the present invention provides testing apparatus for pollution monitoring equipment of a particle detector system, the apparatus comprising:

a flow sensor arrangement adapted to form a sealed fluid communication path between a flow sensor and a sampling inlet of the detector system, wherein the flow sensor determines the flow rate through the sampling inlet so as to allow a determination of an operating condition of the pollution monitoring equipment.

In yet another aspect the present invention provides testing apparatus for testing a particle detector system comprising:

a connector adapted to sealingly engage a sampling inlet of a particle detector system;

a sensing device comprising a flow sensor for conducting an upstream measurement of flow through the sampling inlet, wherein the sensing device is operatively connected to a flow data storage;

an extension means providing sealed fluid communication between the connector and sensing device such that a flow path is formed between the sensing device and the sampling inlet via the connector.

According to embodiments of the above testing apparatus the sensing device further comprises comparator means for comparing a measurement of the flow sensor with a pre-recorded flow measurement of the sampling inlet stored in the flow data storage. An articulated connection may be provided intermediate the connector and extension means for providing relative movement between the connector and extension means. Alternatively, an articulated connection may be provided intermediate the sensing device and extension means for providing relative movement between the sensing device and extension means. The articulated connection preferably comprises a flexible collar. In a preferred embodiment the flow sensor comprises an ultrasonic sensor.

In one form an extension is used to make the connection with the sample inlet from ground level where the flow sensing apparatus measures the flow rate.

In one embodiment the extension used to access the sampling inlet from the ground level may be of an extensible telescopic type, fitted with an air-seal at its junction(s) with the sampling inlet to prevent leakage causing a mis-reading.

Preferably the sensing device of the apparatus further comprises comparator means for comparing a measurement of the flow sensor with a pre-recorded flow measurement of the sampling point stored in the flow data storage.

In a preferred form the flow sensor is an ultrasonic sensor. The ultrasonic sensor preferably measures air flow rate.

In one preferred form the apparatus has an articulated connection intermediate the connector and extension means for providing relative movement between the connector and extension means. Alternatively, the articulated connection may be situated intermediate the sensing device and the extension means. Preferably the articulated connection is a flexible collar.

In still a further aspect the present invention provides a method of field testing a particle detector system, the method comprising the steps of:

connecting a flow sensing apparatus to a sampling inlet of an air sampling system;

measuring the air flow rate into the sampling inlet;

comparing the measured air flow with a previously measured air flow at the time of commissioning the detector system;

determining from the comparative measurements whether a component of the detector system requires maintenance.

In the above field testing method, the component of the detector system may comprise any one or more of:

at least one sampling inlet of an aspirated particle detector system;

a particle detector;

a sampling pipe network of an aspirated particle detector system;

a portion of a sampling pipe network of an aspirated particle detector system;

an aspirated particle detector system.

According to embodiments of the present invention there is also provided apparatus adapted to perform one of:

a) determine an operational condition of a particle detection system;

b) test the operation of pollution monitoring equipment; or c) field test a particle detector system, said apparatus comprising:

processor means adapted to operate in accordance with a predetermined instruction set, said apparatus, in conjunction with said instruction set, being adapted to perform the methods as disclosed herein.

According to embodiments of the present invention there is also provided a computer program product comprising:

a computer usable medium having computer readable program code and computer readable system code embodied on said medium for one of:

a) determine an operational condition of a particle detection system;

b) test the operation of pollution monitoring equipment; or c) field test a particle detector system, within a data processing system, said computer program product comprising:

computer readable code within said computer usable medium for performing the method steps of the methods as disclosed herein.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

This and other embodiments, aspects, advantages and features of the present invention will be set forth in part in the description which follows, and in part will become apparent to those skilled in the art by reference to the following description of the invention and referenced drawings or by practice of the invention. The aspects, advantages and features of the invention are realized and attained by means of the instrumentalities, procedures and combinations particularly pointed out in the appended claims.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limitative of the present invention, and in which.

DETAILED DESCRIPTION

Figure 1:
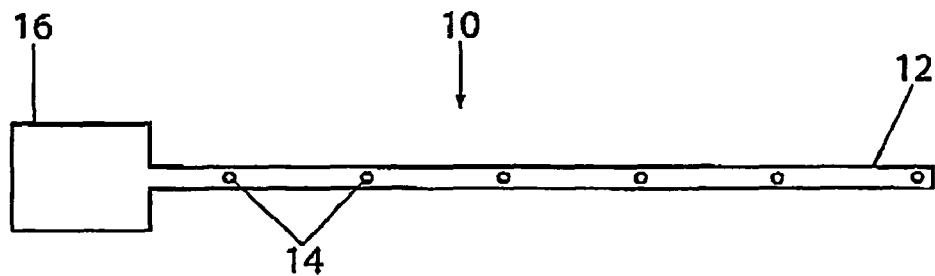
FIG. 1 is a schematic representation of a conventional aspirated particle detection system.

An aspirated particle detection system 10 is shown in FIG. 1, and comprises a pipe 12 having a number of sampling inlets shown as points 14, and a detector 16. The detector may be any type of particle detector, comprising for example a particle counting type system such as a VESDA® LaserPlus™ smoke detector sold by the applicant. Typically the detector 16 comprises a detection chamber, indicator means and an aspirator for drawing sampled air through the pipe into the detection chamber. In operation, each sample point may be placed in a location where smoke detection is required. In this way a sampling point acts to detect smoke in a region.

Figure 2:
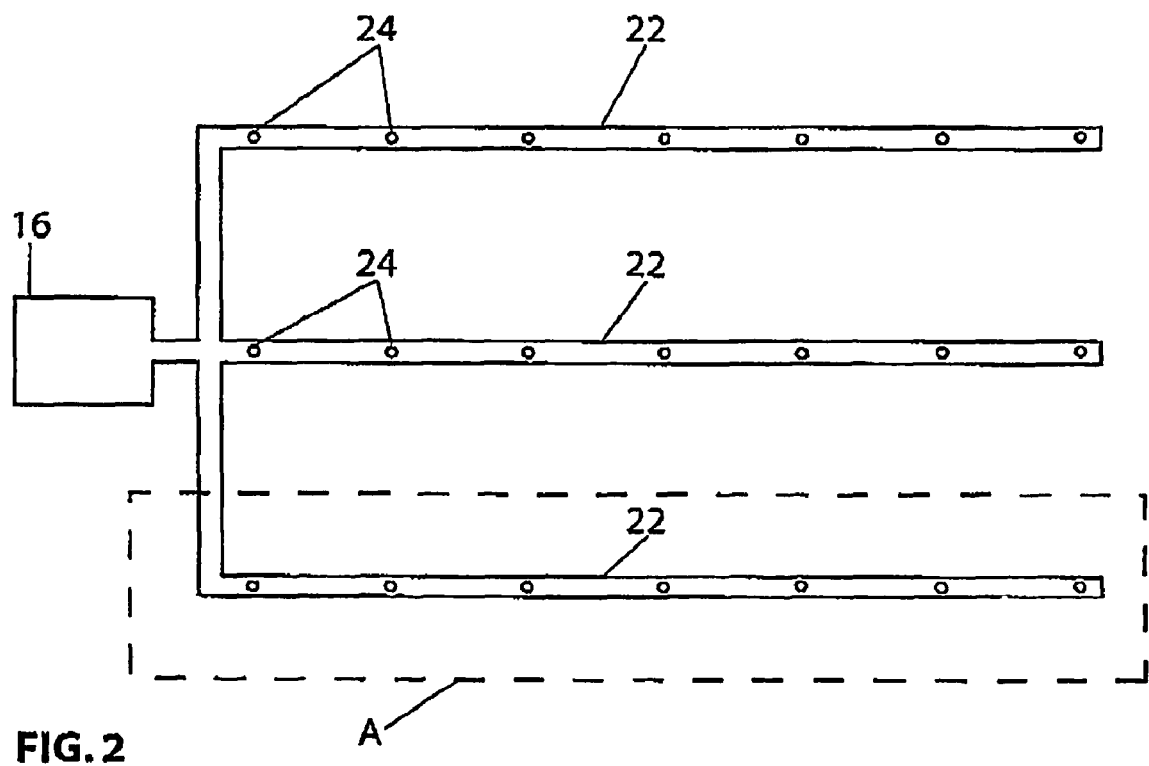
FIG. 2 is a schematic representation of an alternate form of conventional aspirated particle detection system

A second embodiment of a particle detection system is shown in FIG. 2, where a pipe network 20 comprising a number of pipes 22 with sampling points 24 is shown. A similar detector to the detector 16 shown in FIG. 1 may be used. One pipe 22 may consist of a branch, such as branch A in FIG. 2.

In the above systems, air is drawn through sample points 14, 24 and into the pipe 12, 22. The pipe 12 (or 24), will have a number of sampling points 14, (or 24), and therefore air will be drawn through all sampling points within a single pipe when the sampling points are open. Typically during installation all holes are open. If all sampling points are of equal resistance to flow, there are no flow losses along the pipe, and the ambient pressure outside each sample point 14 is the same, then the airflow through all sampling points along pipe 12 will be equal. This results in equal dilution of air from each region to be sampled. Thus, for example, if there are 10 sample inlets, holes 24, and an alarm is to be sounded if smoke of more than 1% obscuration is present in a sample region, then the detector will have to sound an alarm at 0.1% to accommodate the dilution factor of 10 holes for the system as a whole. However, as identified above, in some circumstances, one or more sampling points may block or be in a state of becoming blocked.

It has been discovered that it is not necessary to put smoke or particles into each sampling point to ensure that the smoke or particles will be detected in that region. It is only necessary to detect the flow rate through the sampling point to ascertain whether the sampled air will be drawn into the detection chamber and thus infer that particle sensitivity is conserved in an aspirated particle detector system. For example, if there is no flow through a sample point then the region is not protected. Further, if the flow is too low, then the air from that point will be excessively diluted and smoke or particle detection within the desired levels will not be achieved. Additionally, if flow along a pipe is too low, then transit time for the smoke will exceed requirements.

For example, it has been discovered that a suitable method for determining whether a region is adequately serviced by an aspirated particle detection system is to:

Detect the flow rates through each sample point at a first time (for example after installation, cleaning or repair and, it is noted that, for the purposes of this disclosure, installation may include commissioning);

Detect the flow rates of air through at least some sampling points at some later time (annually or some other regular calendar period such as monthly, bimonthly, half-yearly, biennially etc, or after an incident or some other period);

Compare the flow rates to ascertain whether there has been a significant difference.

In determining whether a significant difference has occurred, the transit time and dilution factors may be taken into account. For example, if the dilution of the air through one sampling point is such that it would not be possible to detect particle in the region at the required level, or the other sampling points became too sensitive, then the sampling point or pipe may require cleaning.

Optionally, a system such as the Aspire™ computer program may be used to determine whether the updated flow rates produce an acceptable result. The Aspire™ computer program is a program that models air flow in an aspirated smoke detector pipe network.

To determine whether the detector itself is working to detect for example, smoke particles, it is only necessary to admit smoke into the system at one sample inlet. If this smoke is detected, then the detector is clearly working. A single release of smoke, as opposed to releases at each and every sample point is easier to control, and typically may be done at the last sampling point on a pipe, where the last sample point is defined as being furthest from the detector.

Figure 3:
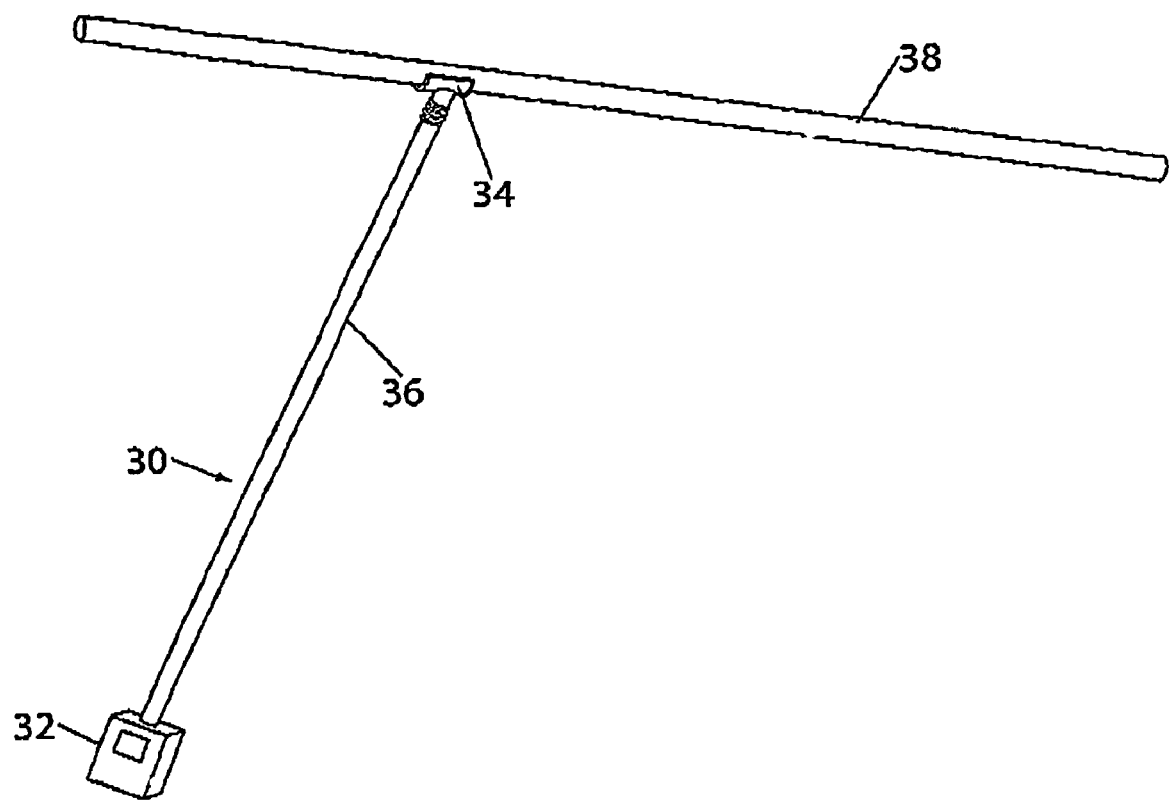
FIG. 3 shows a first embodiment of an apparatus for testing the operation of pollution monitoring equipment in an aspirated particle detector system.

In FIG. 3 a first embodiment of an air sampling particle detector system testing apparatus 30 is shown. Test apparatus 30 comprises a sensing device 32, which itself comprises a flow sensor, a connector 34 and an extension means 36. The connector 34 is adapted to fit over a sampling pipe 38 at a sample point (best shown in FIGS. 4, 5a, 5b and 6). The connector 34 may take a number of forms depending on the type of sampling point used in the aspirated system. Some forms of sampling point are shown in FIGS. 4, 5a, 5b and 6, but the apparatus may be used with a variety of sampling point configurations. The main feature of a connector 34 is that it is adapted to fit a sampling point in a way that provides a reasonable seal. Perfect sealing, while desirable is not required, given the relatively low pressure differentials anticipated in measuring air flow through the sampling points. Sampling points typically have holes from about 2 mm and larger in diameter. Hole 37 represents one form of sample point, while sampling point 38 represents another.

Once the connector 34 is over the sampling point, a flow reading can be made. If the sampling point is not blocked, and the aspirator is operational, some air will be drawn through the sample hole. The flow sensor may take a number of forms, but in the preferred embodiment an ultrasonic flow meter is used. The ultrasonic flow meter comprises two transducers spaced apart by a known distance, exposed to but not necessarily in the air flow into the sampling point. The flow is detected by measuring time of flight of an ultrasound waveform or signal transmitted from one transducer to another, in a manner described in the Applicant company's International Patent Application No PCT/AU2004/00639. The use of ultrasonic transducers allows for accurate measurement of airflow, while providing low resistance to air flow, as the transducers do not need to project into the airstream. The flow sensor outputs a reading, for example in liters of air per minute, to the user, and/or stores the reading in a memory device (not shown). This data may then be correlated to data collected from previous tests.

If a sampling point is blocked, it maybe cleaned by known instruments such as a pipe cleaner.

It is also possible to detect airflow down a branch of a pipe network (such as branch A in FIG. 2), by detecting airflow through the sample holes 24 in that branch. This method is useful for determining whether the pipe may have leaks, blockages not related to a single sampling point, or other external issues such as variations in ambient pressure between branches.

Flow impedance of the extension means 36 and the test apparatus 30 in general must be sufficiently low to have a negligible effect on the flow being measured through the sample point. Preferably the test apparatus 30 is hand-held, light weight, and powered by internal batteries. Typical flow rates in a sampling point are in the region of 2 liters per minute; but this may vary. The preferred flow reading accuracy should be approximately 0.1 liters per minute or 10% of reading, whichever is the greater. Pressure drops across the sampling hole may be as low as 25 Pascals so the extension means, preferably in the form of a tube, and sensing device should ideally not produce a combined pressure drop of, for example, more than 2.5 Pascals. As an example a tube inner diameter of 21 mm for the extension means 36 will ensure a suitably low pressure loss at a flow rate of 2 liter/min in a tube of up to 6 m length.

Figure 4:
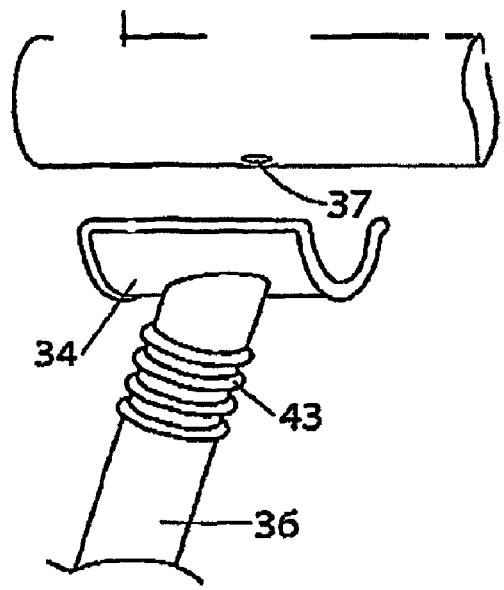
FIG. 4 shows a part of the apparatus of FIG. 3 with a sample pipe of an aspirated particle detector system.
Figure 5A:
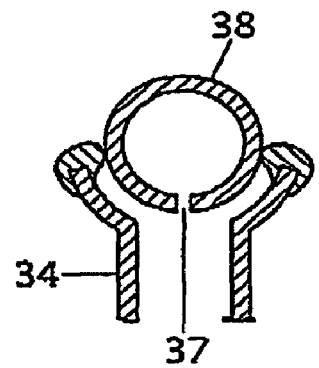
FIGS. 5a and 5b show a cross section of the testing apparatus in use with a sampling pipe of an aspirated particle detector system in accordance with further embodiments of the invention.
Figure 6:
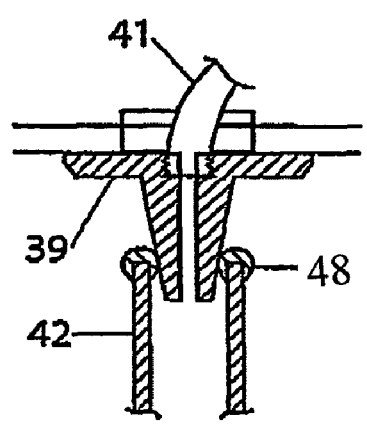
FIG. 6 shows a portion of yet a further embodiment of a test apparatus in use with a sampling point of a sampling pipe of an aspirated particle detector system.
Figure 5B:
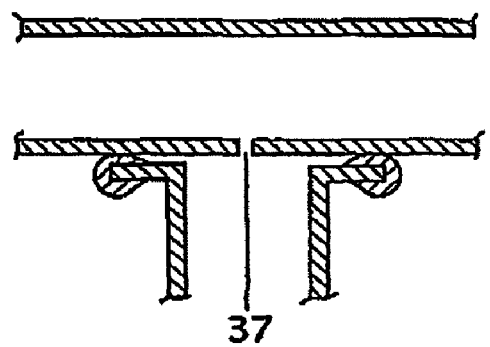

To ensure a low-leakage air seal to the sampling point the end of the tube may be fitted with a suitably shaped soft seal; eg made of rubber, neoprene or the like. Examples are shown in FIGS. 4-6. Typically there are 2 commonly used style of sampling points in aspirated particle detectors, also shown in FIGS. 4-6.

The first type of sample point 37 is a simple hole drilled in a sampling pipe 38. Typically the hole 37 may be of 3 mm diameter, while a pipe 38 may be of 25 mm outer diameter; though these figures will vary from design-to-design and from region-to-region. To accommodate this the connector 34 for the pipe 38 may be fitted with a pick-up head of a trough-like shape, U-shaped in cross section, with a seal around the rim.

The second style of sampling point is typically in the form of a nozzle 39 connected to the sample pipe 38 by a length of relatively narrow flexible hose 41. Referring to FIG. 6, to accommodate this, the end of the extension 36 may be fitted with a pick-up head 42 of a simple ring shape, with a seal 48 around the rim. In the case of some interfaces, a taper fit alone may be adequate, without the need for a soft seal.

In all cases the seal 48 may be either a different material or the same material as the connector.

Optionally, the uppermost part of the tube 36, intermediate the connector 34 and the extension means 36, may be fitted with a flexible section to allow the pick-up head to mate properly with the sampling point even though the tube is not held entirely perpendicular to the sampling pipe. A flexible section 43 is shown in FIG. 4. Alternatively, the flexible section 43 may be fitted intermediate the sensing device 32 and the extension means 36.

Other styles of sampling point may be accommodated by minor variations on the same general approach.

As the present invention may be embodied in several forms without departing from the spirit of the essential characteristics of the invention, it should be understood that the above described embodiments are not to limit the present invention unless otherwise specified, but rather should be construed broadly within the spirit and scope of the present invention as defined in the appended claims. Various modifications and equivalent arrangements are intended to be included within the spirit and scope of the present invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof." Thus, unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The invention claimed is:

1. A method for determining an operational condition of a particle detection system, the particle detection system comprising a plurality of sample inlets for receiving a plurality of sample flows from a monitored region, the method comprising the steps of:
   providing a flow sensor and a single extension means;
   conducting an upstream measurement of a flow rate through one sample inlet using the flow sensor and the single extension means such that the measuring is performed at a point at or near ground level that is remote from the sampling inlet; and
   determining an operational condition of the particle detection system in accordance with the measured flow rate;
   wherein the step of conducting an upstream measurement is repeated for at least one more of the sample inlets using the flow sensor and the single extension means.

2. The method as claimed in claim 1 wherein the step of measuring the flow rate is performed using an ultrasonic flow sensor.

3. The method as claimed in claim 1 wherein the operational condition comprises one or more of:
   particle detection system sensitivity;
   particle detector sensitivity;
   sampling pipe network obstruction;
   sampling inlet obstruction.

4. An apparatus adapted to perform one of:
   determine an operational condition of a particle detection system;
   test the operation of pollution monitoring equipment; or
   field test a particle detector system, said apparatus comprising:
   processor means adapted to operate in accordance with a predetermined instruction set,
   said apparatus, in conjunction with said instruction set, being adapted to perform the method as claimed in claim 1.

5. A computer program product comprising:
   a non-transitory computer usable medium having computer readable program code and computer readable system code embodied on said medium for one of:
   determine an operational condition of a particle detection system;
   test the operation of pollution monitoring equipment; or
   field test a particle detector system, within a data processing system, said computer program product comprising:
   computer readable code within said computer usable medium for performing the method steps of claim 1.

6. The method of claim 1, wherein the particle detection system includes a pipe in which said plurality of sample inlets are provided and a particle detector downstream of the plurality of sample inlets.

7. A method of testing the operation of pollution monitoring equipment, the pollution monitoring equipment comprising a particle detection system, the particle detection system comprising a plurality of sample inlets for receiving a plurality of sample flows from a monitored region, the method comprising the steps of:
   providing a flow sensor and a single extension means;
   measuring the upstream flow rate through one sampling inlet of the particle detector system using the flow sensor;
   determining an operational condition of the pollution monitoring equipment in accordance with the measured flow rate;
   wherein the step of measuring the upstream flow rate includes using the single extension means such that the measuring is performed at a point at or near ground level that is remote from the sampling inlet; and
   wherein the step of measuring the upstream flow rate is repeated for at least one more of the sample inlets using the flow sensor and the single extension means.

8. The method as claimed in claim 7 further comprising the steps of:
   repeating the step of measuring the upstream flow rate through respective sample inlets after a predetermined time interval;
   determining the operational condition by comparing respective flow rate measurements for each of the sample inlets.

9. The method as claimed in claim 8 wherein the predetermined time interval comprises one or more of:
   the occurrence of an incident;
   the occurrence of a maintenance action;
   regular calendar periods.

10. The method as claimed in claim 8, wherein:
    the step of measuring the upstream flow rate, in the first instance, is performed upon one of:
    installation;
    cleaning; and
    repair of the pollution monitoring equipment.

11. The method as claimed in claim 7, wherein the pollution monitoring equipment comprises one or more of:
    a plurality of sampling inlets of an aspirated particle detector system;
    a particle detector;
    a sampling pipe network of an aspirated particle detector system;
    a portion of a sampling pipe network of an aspirated particle detector system;
    an aspirated particle detector system.

12. The method of claim 7, wherein the particle detection system includes a pipe in which said plurality of sample inlets are provided and a particle detector downstream of the plurality of sample inlets.

13. A testing apparatus for pollution monitoring equipment of a particle detector system, the apparatus comprising:
- a flow sensor arrangement adapted to form a sealed fluid communication path between a flow sensor and one of a plurality of sampling inlets of the detector system, wherein the flow sensor determines the flow rate through the sampling inlet so as to allow a determination of an operating condition of the pollution monitoring equipment;
- wherein the flow sensor arrangement includes the flow sensor and a single extension means between the flow sensor and the sampling inlet; and
- wherein the flow sensor arrangement is adapted to form, in turn, a sealed fluid communication path with respective sampling inlets of the detector system.

14. The apparatus as claimed in claim 13 wherein the pollution monitoring equipment comprises one or more of:
- a plurality of sampling inlets of an aspirated particle detector system;
- a particle detector;
- a sampling pipe network of an aspirated particle detector system;
- a portion of a sampling pipe network of an aspirated particle detector system;
- an aspirated particle detector system.

15. The apparatus as claimed in claim 14 wherein the sensing device further comprises comparator means for comparing a measurement of the flow sensor with a prerecorded flow measurement of each of the sampling inlets stored in the flow data storage.

16. The apparatus as claimed in claim 13 wherein the flow sensor comprises an ultrasonic sensor.

17. The testing apparatus of claim 13, wherein the particle detection system includes a pipe in which said plurality of sample inlets are provided and a particle detector downstream of the plurality of sample inlets.

18. A testing apparatus for testing a particle detector system comprising:
- a connector adapted to sealingly engage one of a plurality of sampling inlets of a particle detector system;
- a sensing device for testing flow rate through the sampling inlet of the particle detector system, the sensing device comprising a flow sensor for conducting an upstream measurement of flow through the sampling inlet, wherein the sensing device is operatively connected to a flow data storage;
- a single extension means providing sealed fluid communication between the connector and sensing device such that a flow path is formed between the sensing device and the sampling inlet via the connector;
- wherein the fluidly sealed connector, single extension means, and sensing device are adapted to sealingly engage respective sampling inlets of the particle detector system.

19. A testing apparatus for testing a particle detector system comprising:
- a connector adapted to sealingly engage one of a plurality of sampling inlets of a particle detector system;
- a sensing device for testing flow rate through the sampling inlet of the particle detector system, the sensing device comprising a flow sensor for conducting an upstream measurement of flow through the sampling inlet, wherein the sensing device is operatively connected to a flow data storage;
- a single extension means providing sealed fluid communication between the connector and sensing device such that a flow path is formed between the sensing device and the sampling inlet via the connector;
- wherein the connecting device is adapted to sealingly engage respective sampling inlets of the particle detector system;
- and wherein the apparatus further comprises an articulated connection intermediate the connector and extension means for providing relative movement between the connector and extension means.

20. The apparatus as claimed in claim 19 wherein the articulated connection comprises a flexible collar.

21. A testing apparatus for testing a particle detector system comprising:
- a connector adapted to sealingly engage one of a plurality of sampling inlets of a particle detector system;
- a sensing device for testing flow rate through the sampling inlet of the particle detector system, the sensing device comprising a flow sensor for conducting an upstream measurement of flow through the sampling inlet, wherein the sensing device is operatively connected to a flow data storage;
- a single extension means providing sealed fluid communication between the connector and sensing device such that a flow path is formed between the sensing device and the sampling inlet via the connector;
- wherein the connecting device is adapted to sealingly engage respective sampling inlets of the particle detector system;
- and wherein the apparatus further comprises an articulated connection intermediate the sensing device and extension means for providing relative movement between the sensing device and extension means.

22. A method of field testing a particle detector system, the method comprising the steps of:
- connecting a flow sensing apparatus including a single extension means to one of a plurality of sampling inlets of an air sampling system;
- measuring the air flow rate into the sampling inlet;
- comparing the measured air flow with a previously measured air flow at the time of commissioning the detector system;
- determining from the comparative measurements whether a component of the detector system requires maintenance;
- detecting the flow sensing apparatus from the sampling inlet; and
- repeating the connecting step with the flow sensing apparatus for at least one or more of the plurality of sampling inlets and subsequently performing the measuring, comparing, and determining steps.

23. The method as claimed in claim 22 wherein the component of the detector system comprises any one or more of:
- a plurality of sampling inlets of an aspirated particle detector system;
- a particle detector;
- a sampling pipe network of an aspirated particle detector system;
- a portion of a sampling pipe network of an aspirated particle detector system;
- an aspirated particle detector system.

24. An apparatus adapted to perform one of:
   determine an operational condition of a particle detection system;
   test the operation of pollution monitoring equipment; or
   field test a particle detector system, said apparatus comprising:
   processor means adapted to operate in accordance with a predetermined instruction set, said apparatus, in conjunction with said instruction set, being adapted to perform the method as claimed in claim 22.

25. A computer program product comprising:
   a non-transistory computer usable medium having computer readable program code and computer readable system code embodied on said medium for one of:
   determine an operational condition of a particle detection system;
   test the operation of pollution monitoring equipment; or
   field test a particle detector system, within a data processing system, said computer program product comprising:
   computer readable code within said computer usable medium for performing the method steps of claim 22.

26. The method of claim 22, wherein the particle detection system includes a pipe in which said plurality of sample inlets are provided and a particle detector downstream of the plurality of sample inlets.

\* \* \* \* \*